(12) United States Patent
Kaufman

(10) Patent No.: US 7,375,357 B2
(45) Date of Patent: May 20, 2008

(54) PERMANENT MAGNET RADIATION DOSE DELIVERY ENHANCEMENT

(75) Inventor: Leon Kaufman, San Francisco, CA (US)

(73) Assignee: Avi Faliks, Allendale, NJ (US)

( * ) Notice: Subject to any disclaimer, the term of this patent is extended or adjusted under 35 U.S.C. 154(b) by 283 days.

(21) Appl. No.: 11/209,447

(22) Filed: Aug. 23, 2005

(65) Prior Publication Data

US 2006/0049902 A1 Mar. 9, 2006

Related U.S. Application Data

(60) Provisional application No. 60/604,090, filed on Aug. 23, 2004.

(51) Int. Cl.
*H01J 1/50* (2006.01)
(52) U.S. Cl. .................. 250/492.3; 250/400; 250/398; 250/396 ML
(58) Field of Classification Search ............. 250/492.3, 250/396 ML
See application file for complete search history.

(56) References Cited

U.S. PATENT DOCUMENTS

| | | | | |
|---|---|---|---|---|
| 5,672,879 | A * | 9/1997 | Glavish | 250/396 ML |
| 5,974,112 | A | 10/1999 | Reiffel | |
| 6,663,555 | B2 | 12/2003 | Mitchiner et al. | |
| 6,670,877 | B2 * | 12/2003 | Rapoport | 335/296 |
| 6,961,620 | B2 * | 11/2005 | Rioux et al. | 607/99 |
| 2004/0162457 | A1 * | 8/2004 | Maggiore et al. | 600/1 |

OTHER PUBLICATIONS

Becchetti, F.D. et al., "Magnetic confinement of radiotherapy beam-dose profiles," *Cyclotrons and Their Applications 2001, Sixteenth International Conference, American Institue of Physics*, 3 pages (2001).

Chu, J. et al., "The use of magnetic fields to improve photon dose distributions for radiation therapy—a possible approach to "poor man's proton" beam properties," *Digest of Papers of the 2000 World Congress on Medical Physics and Biomedical Engineering and the Proceedings of the 22nd Annual International Conference of the IEEE Engineering in Medicine and Biology Society*, Chicago, 2000, 4 pages.

Earl, M. and Ma, L., "Depth dose enhancement of electron beams subject to external uniform longitudinal magnetic fields: a Monte Carlo Study," *Med. Phys.*, 29:484-491 (Apr. 2002).

Jette, D., "Magnetic fields with photon beams: Use of circular current loops," *Med. Phys.*, 28:2129-2138 (Oct. 2001).

Lee, M., and Ma, C.M., "Monte Carlo characterization of clinical electron beams in transverse magnetic fields," *Phys. Med. Biol.*, 45:2947-2967 (2000).

(Continued)

*Primary Examiner*—Jack I. Berman
*Assistant Examiner*—Andrew Smyth
(74) *Attorney, Agent, or Firm*—Townsend and Townsend and Crew LLP

(57) ABSTRACT

The present invention provides a plurality of permanent magnets to enhance radiation dose delivery of a high energy particle beam. The direction of the magnetic field from the permanent magnets may be changed by moving the permanent magnets.

43 Claims, 7 Drawing Sheets

OTHER PUBLICATIONS

Litzenberg, D. et al., "Experimental apparatus to measure the effects of strong longitudinal magnetic fields on photon and electron radiotherapy beams," Submitted to *Phys. Med. Bio.*, Nov. 2000, <http://www.physics.Isa.umich.edu/twinsol/Publications/Magcnfpreprint11_00.pdf.>, pp. 1-10 (Mar. 2, 2006).

Nardi, E. and Barnea, G., "Electron beam therapy with transverse magnetic fields," *Med. Phys.*, 26:967-973 (Jun. 1999).

Nath, R. and Schultz, R.J., "Modification of electron-beam dose distributions by transverse magnetic fields," *Med. Phys.*, 5:226-230 (May-Jun. 1978).

Paliwal, B. et al., "Magnetic field modification of electron-beam dose distributions in inhomogeneous media," *Med. Phys.*, 5:404-408 (Sep.-Oct. 1978).

Paliwal, B. et al., "Magnetic modification of electron beam dose distributions," *Acta. Radiol. Oncol. Radiat. Phys. Biol.*, 18:57-64 (1979).

Reiffel, L. et al., "Control of photon beam dose profiles by localized transverse magnetic fields," *Phys. Med. Biol.*, 45:N177-N182 (2000).

Shih, C.C., "High energy electron radiotherapy in a magnetic field," *Med. Phys.*, 2:9-13 (Jan.-Feb. 1975).

Wadi-Ramahi, S. et al., "Evaluating the effectiveness of a longitudinal magnetic field in reducing underdosing of the regions around upper respiratory cavities irradiated with photon beams—A Monte Carlo study," *Med. Phys.*, 28:1711-1717 (Aug. 2001).

Weinhous, M. et al., "Enhancement of electron beam dose distributions by longitudinal magnetic fields: Monte Carlo simulations and magnet system optimization," *Med. Phys.*, 12:598-603 (Sep.-Oct. 1985).

Whitmire, D. et al., "Magnetic modification of the electron-dose distribution in tissue and lung phantoms," *Med. Phys.*, 5:409-417 (Sep.-Oct. 1978).

Whitmire, D. et al., "Magnetic enhancement of electron dose distribution in a phantom," *Med. Phys.*, 4:127-131 (Mar.-Apr. 1977).

* cited by examiner

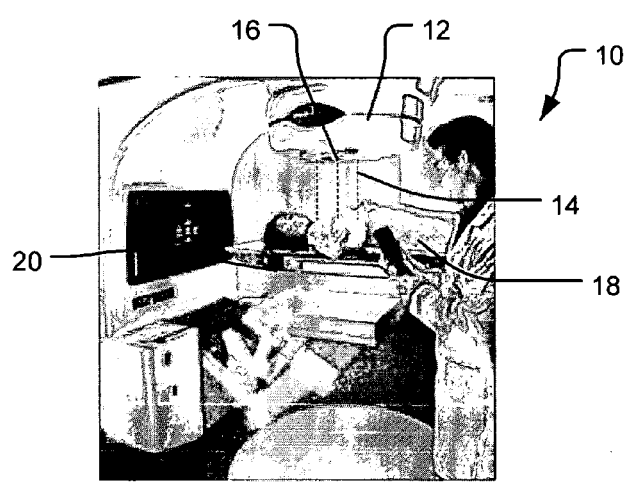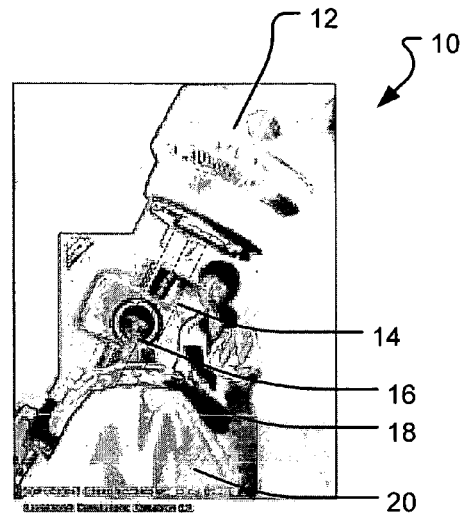
FIG. 1A
FIG. 1B
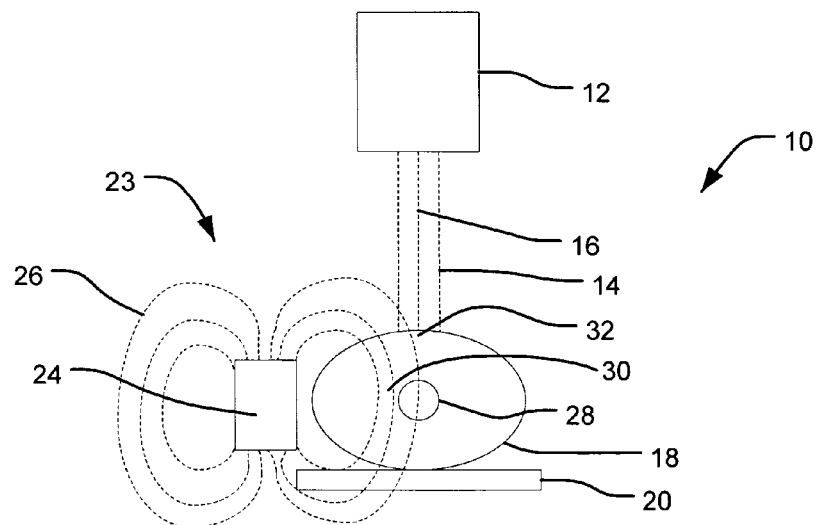
FIG. 1C

PERMANENT MAGNET RADIATION DOSE DELIVERY ENHANCEMENT

CROSS REFERENCE TO RELATED APPLICATIONS

The present invention claims benefit to U.S. provisional patent application Ser. No. 60/604,090, filed Aug. 23, 2004 the complete disclosure of which is incorporated herein by reference.

BACKGROUND OF THE INVENTION

The present invention relates generally to providing and controlling dose enhancements in high energy particle beam (electrons or photons) treatment of a target area in a patient's body. More specifically, the present invention relates to methods and systems that use a permanent magnet assembly that creates a dose enhancement at the target area along the high energy particle beam path, compared to the dose delivered to surrounding regions of the patient's body along the beam path.

A photon beam interacts with tissue in a well-understood manner. Photons themselves, whatever their energy, do not produce ionization (e.g., damage). Rather, the photons interact with the electrons and nuclei of tissue constituents. This interaction results mostly in electrons (and positrons) receiving a substantive amount of energy from the photon beam. These moving charged particles are responsible for the ionization that damages the tissue.

The angular distribution of the electrons initially depends on the energy of the photons, but scattering interactions lead to more photons, that then result in more electrons, in what is called a "cascade," that generates a path of ionizing particles that becomes broader and the process becomes diffusive. These effects have two results that impact the effectiveness of radiation treatment with photon beams. First, the initial photon beam target area is not well defined, being mostly dependent on the density of the tissue in its path, with a component due to attenuation, i.e., less beam is left the deeper it penetrates into the subject. Second, the cascade further results in dose delivery downstream to the target area, as well as outside the beam boundary.

Similar considerations apply to electron beams used in radiation treatment. As the electron travels through tissue, it produces ionization along its entire path, losing small amounts of its energy to each ionization. It can also undergo scattering with an electron (or nucleus) in the tissue, and this scattering transfers a large fraction of its energy. Once an electron interacts with the tissue in this manner, a cascade of electrons and photons is produced, which, qualitatively, is not different from that produced by a photon.

Radiation therapy planning is a mature, yet still evolving practice. During radiation therapy, an operator will typically manipulate a beam profile and/or beam directions to attempt to maximize the radiation dosage to the target area(s), while minimizing the amount of radiation dosage to the surrounding and non-adjacent tissue in the patient body.

The actual path of photon beams cannot be affected in a measurable manner. On the other hand, the path of charged particles is affected by electric and magnetic fields, a phenomenon used in CRTs, for example. For practical reasons, magnetic fields are generally preferable for this purpose. For any given magnetic (or electric) field strength the effect on the path of the beam will be lower for higher particle energy, thus the beam of electrons will be much less affected than the cascade electrons. A moving charged particle in a magnetic field will see a force perpendicular to its direction of motion and perpendicular to the magnetic field vector, so that it will tend to circle the magnetic field line. This results in a corkscrew motion where speed is preserved, but the velocity vector has a component along the field lines and another component around the field lines. In the absence of impediments, the electrons will travel along magnetic field lines and diffuse towards the region with the weakest magnetic field and away from the strong magnetic field region.

To that end, Whitmire et al., "Magnetic modification of the electron-dose distribution in tissue and lung phantoms," Med. Phys 5(5), September/October 1978 (the complete disclosure of which is incorporated by reference) describes the use of an electromagnet to generate a moderately strong transverse-magnetic field to modify electron-dose distributions in tissue, and discusses the use of superconducting magnets for the same purpose. Lee and Ma, "Monte Carlo characterization of clinical electron beams in transverse magnetic fields," Phys. Med. Biol. 45(10):2947-2967, 2000 (the complete disclosure of which is incorporated by reference) studied the characteristics of the electron beam of a clinical linear accelerator in the presence of 1.5 and 3.0 Tesla transverse magnetic fields to assess the possibility of using magnetic fields in conjunction with modulated electron radiation therapy. Longitudinal magnetic fields have also been found to enhance the depth of dosage distribution of an electron beam when the field was applied prior to the beam reaching the target. (Earl and Ma, Med. Phys. 29(4):484-491, 2002, the complete disclosure of which is incorporated by reference).

Similarly, U.S. Pat. No. 5,974,112 to Reiffel, the complete disclosure of which is incorporated herein by reference, describes a method of controlling and enhancing dose in the target area of a patient's body by using a topical magnet in the form of an array of magnet coils to create a magnetic field within a subject undergoing radiation therapy. As described in Reiffel, the magnet is characterized as producing a "magnetic field configuration having a magnetic field component across the beam path and having a magnetic field gradient component along the beam path which cause the dose enhancement, the dose enhancement being changeable during beam use by changing the magnetic field configuration during beam use, wherein the topical magnetic field can be produced by an array of magnet coils." In one particular embodiment, Reiffel suggests using superconducting magnet coils. In a separate study, Reiffel et al. examined the effects of a small super conducting magnet on the control over photon dose effects. (Phys. Med. Biol. 45:N177-N182, 2000, the complete contents of which is incorporated herein). In water phantoms, Reiffel et al. found that the effects of a locally strong transverse magnetic field with large gradients extended to 3 to 4 cm or more beyond the warm face of the cryostat.

Currents in superconductors and normal conductors may be used to produce magnetic fields of distributions calculable from well known physical principles. In practice, however, both normal conductors and superconductor coils are impractical for enhancing dosage in a photon and electron beam treatment to a target area in a patient's body.

Conventional resistive coil magnets generate a large amount of heat from the currents used to create the magnetic field. The heat is typically controlled by using thicker conductors for the coils (e.g., less resistance) and using active water cooling. For high magnetic fields, the magnetic coils are very large and cumbersome and electrical consumption is high. Because of the cumbersome nature and need for active cooling, the coils are difficult to reposition and reorient. Furthermore, they are large and the coil magnets need to be positioned relatively far away from the patient, thus limiting its ability to create sufficient magnetic fields within the patient's body (the field strength drops rapidly with distance from the magnet).

While the use of superconducting coil magnets eliminate the heat dissipation problem, the superconducting coils have the additional requirement of needing to be kept cold, typically between about 4 Kelvin and 10 Kelvin. Such cooling typically requires a liquid helium circulating system or active cryogenic coolers (operated by electricity, and also generating heat that needs to be dissipated). The whole assembly has to be kept within a vacuum cryostat. Typically, between the superconducting coil and the outside vacuum cryostat, there is an intermediate temperature shield (40 to 77 Kelvin) kept cold by liquid nitrogen or an active cryogenic cooler. Some cooling systems are dry (only an electric cooler), some are liquid (helium and nitrogen), and others hybrid, and use the active cooler to preserve the cryogenic liquids. Typically, multiple layers of superinsulation (aluminized Mylar) are placed between the superconducting coils and the shield, and between the shield and the vacuum cryostat. Care must be taken that the superinsulation does not touch the cryostat and provide heat conducting paths (called heat shorts). Consequently, the superconducting coil magnet assembly is a bulky system, and one that needs to be fabricated with great care and maintained both at vacuum and low temperature continuously, whether in use or not. A particular disadvantage is the space introduced between the magnetic field-generating coils and the outside of the cryostat, this space taken up by two superinsulation blankets, the intermediate shield, and the low temperature container, the intermediate temperature container and the room temperature container. This space reduces the magnetic field strength at the patient.

In another aspect of this practice, for superconducting magnets, considerations of restrictions on winding of the wire and the need for cooling and insulation, restrict the practically achievable magnetic field configurations. The winding of superconducting coils for achieving high fields is an art. Winding configurations are limited by the need to avoid sharp bends and to minimize stresses on the wire. The stresses arise from the interaction of the current in the coil with the magnetic field the current creates. When winding shapes depart from the perfectly circular, even if they are elliptical, these problems start to exacerbate. Therefore, for practical purposes, most magnets are typically limited to simple circular confirmations.

The topical superconducting magnets, because of winding, cooling and insulation constraints, if unobtrusive, typically lend themselves only to the creation of non-uniform fields, all with the basic topology of a dipole. While proven useful, these magnetic fields are less than optimal.

From the above, it is apparent that improvements over the array of coil magnet are needed. In particular, what are needed are low cost, simple systems and methods which enhance a radiation dose to a target area in comparison to the radiation dose to the surrounding regions in the patient's body. Preferably, the methods and systems should be robust and easily reconfigurable.

BRIEF SUMMARY OF THE INVENTION

The present invention provides methods, devices and systems for dose enhancement in high energy particle beam treatment of a target area in a patient's body using a permanent magnet assembly that comprises one or more permanent magnets. The dosage of the high energy particle beam delivered to the desired target area is enhanced in comparison to the radiation dose delivered to the surrounding regions. The permanent magnet assembly of the present invention is stable, easy to manufacture, is maintenance free, is not prone to failure, and can reproduce any magnetic field produced by the coil magnets. Because there is no current running through the permanent magnet assembly, the permanent magnet assembly is unconstrained by winding limitations, cooling or insulators, and is easily reconfigurable and repositionable.

The permanent magnet assembly may be positioned near the target to create a magnetic field that is substantially parallel to the high energy particle beam. A magnetic field parallel to the high energy particle beam will have as its main effect to limit radial diffusion of electrons, and make the radial dose profile of the beam more closely conform to the beam cross-sectional shape of the beam.

Additionally, the permanent magnet assembly may also be positioned (or repositioned) to create a magnetic field that is transverse to the high energy particle beam. A magnetic field transverse to the beam will have less effect on radial profiles (one direction will be shielded and another will be enhanced), but will tend to reduce dose buildup downstream from the target area.

As can be appreciated, the permanent magnet assembly of the present invention may also be positioned to create a magnetic field that is more than 0-degrees angled with respect to beam path and less than 90-degree angle with respect to the transverse plane of the beam path. Such magnetic fields will produce some confinement along the beam and some along transverse directions, but will allow dose to "leak" along the field direction.

Reconfiguration of the magnetic field produced by the permanent magnet assembly may be carried out by moving the permanent magnet assembly relative to the body, the permanent magnets relative to each other, or by moving ferromagnetic elements relative to the permanent magnet(s). A control system of the radiation system may be preprogrammed with known geometric configurations of the permanent magnet assembly that create known magnetic fields.

In one aspect, the present invention provides a radiation treatment system that comprises a beam source (e.g., an electron beam source or a photon beam source) that generates a beam of high energy particles along a beam path directed toward a body. A permanent magnet assembly that comprises at least one permanent magnet generates a magnetic field that causes a dose enhancement in a desired target area of the body compared to surrounding regions or in other regions of the body along the beam path. The dose enhancement provided by the permanent magnets of the present invention will depend on the field strength, the shape, and orientation of the permanent magnets.

The permanent magnet(s) may be comprised of a variety of different materials. For example, the permanent magnet(s) may comprise NdFeB, Alnico, SmCo, ferrites, or the like. Due to the ease in manufacturing of permanent magnets, the permanent magnets can be in a variety of different sizes and shapes. The permanent magnets are typically formed from shaped blocks of magnetic material, but if desired, a plurality of magnetized tiles may be used to create a complex three-dimensional array of magnets so as to create a desired magnetic field.

The permanent magnet assembly may comprise a single permanent magnet that creates a dipole magnetic field in the body, or it may comprise a plurality of permanent magnets that creates a more complex magnetic field in the body. The single permanent magnet may be adapted to have a configurable geometry so as to allow for a modification of the dipole field relative to the beam path and the body. For example, the permanent magnet may be coupled to a movement controller to allow for linear movement and/or rotation of the permanent magnet. Movement of the permanent magnet can move the magnetic field so as to align the magnetic field between being substantially parallel with the beam path and being substantially orthogonal to the beam path. The movement controller can be manually activated or computer controlled.

The system may further comprise a one or more additional elements (e.g., ferromagnetic element and/or additional permanent magnets) that may be used to modify the magnitude (direction and/or size) of the magnetic field that is generated in the patient's body. At least one of the permanent magnet and the additional element (e.g., ferromagnetic element and additional permanent magnet) may be movable relative to the beam path and patient's body. In some embodiments both the permanent magnet and the additional element are movable. In other embodiments, only one of the permanent magnet and the additional element is movable.

The relative movement of the permanent magnet and/or the additional elements relative to the patient's body and beam path changes the geometry of the permanent magnet assembly. The changed geometry changes the magnetic field. As can be appreciated, any change to the magnetic field in the body will change the effect on the dose enhancement.

In one particular embodiment, the permanent magnet assembly comprises a toroidal permanent magnet and a cylindrical first element disposed within an opening of the toroidal permanent magnet. The first element may be a ferromagnetic material or a permanent magnet. Optionally, a second element (ferromagnetic magnet or permanent magnet) in the form of a toroid or annulus may be concentrically disposed around the toroidal permanent magnet. A third element (ferromagnetic magnet or permanent magnet) in the form of a partial ring or other asymmetrical shape, may be disposed around the toroidal element. The elements (and typically all of the elements) are movable relative to each other and movable relative to the beam path and the patient's body so as to change the geometry of the permanent magnet assembly so as to allow for reconfiguration of the magnetic field. The same arrangement could be assembled with elliptical, square, rectangular or triangular shapes instead of toroidal shaped.

The movement controller may be coupled to both the beam source and the permanent magnet(s). In one usage, the movement controller may be programmed so that the beam source and permanent magnet(s) are synchronously moved so as to maintain the relative position between the permanent magnet(s) and the beam path. In another usage, the movement controller is programmed to reorient at least one permanent magnet about one or more axes (independent of the movement of the beam source) so as to modify the magnitude (direction and/or strength) of the magnetic field generated by the permanent magnet, relative to the body and beam path. The movement controller of the present invention may be programmed to move the permanent magnet and additional elements to any number of preset positions relative to the beam path and patient's body to generate known magnetic fields.

A support assembly may movably position the permanent magnet assembly on one side of the patient's body and a pole piece on a substantially opposite side of the patient's body. The support assembly is typically C-shaped or U-shaped. The support assembly itself may be comprised of a ferromagnetic material so as to concentrate the magnetic field from the permanent magnets. The pole piece may comprise a permanent magnet or a ferromagnetic material. Additionally, the pole piece may comprise a plurality of ferromagnetic material elements or a plurality of permanent magnets. Movement of the plurality of permanent magnets or ferromagnetic elements may be used to concentrate or distribute the magnetic field, as desired. In one embodiment, the pole piece comprises a plurality of wedge, triangular, or pie-shaped elements.

In other embodiments of the present invention, a catheter or probe that comprises a permanent magnet assembly may be introduced into the body to protect desired regions of the body during a radiation therapy procedure.

In another aspect of the present invention, the present invention provides a method of enhancing target radiation dose in medical treatments. The method comprises directing a high energy particle beam at a body along a beam path and orienting a permanent magnet assembly that comprises at least one permanent magnet adjacent a target tissue to create a magnetic field component in the body, wherein the at least one permanent magnet enhances a radiation dose in a target area of the body, compared to surrounding regions or in other regions of the beam along the beam path. In the present application, the term "dose enhancement" or 'enhancement" refers to an increase in the ratio of radiation dose delivered to a target area as compared to a non-target tissue that is desirable to protect. The radiation dose to the target for a given input radiation beam intensity may increase, be unchanged, or be reduced by the use of the methods of the present invention.

The high energy particle beam may be an electron beam or a photon beam. The permanent magnet(s) may be moved and/or rotated so as to change the geometry of the permanent magnet assembly and to change the magnet field component in the patient's body. Optionally, the permanent magnet may be synchronously rotated with the beam source so as to maintain the relative position between the beam path and the permanent magnet(s). Changing the geometry is typically carried out by moving the permanent magnet(s) relative to each other and/or the patient's body and beam path. Simple rotation of the permanent magnet so that the poles are oriented differently relative to the patient's body will change the magnetic field vector within the patient's body.

A first element (such as an additional permanent magnet or a ferromagnetic material) may be used to modify the magnetic field in the body. For example, moving at least one of the first element and the permanent magnet relative to the body modifies the magnetic field. To further modify the magnetic field within the body, a movable second element, third element, . . . $n^{th}$ element, may be provided to customize the magnetic field in the body.

In one embodiment, the permanent magnet comprises a toroidal permanent magnet and the first element is cylindrical and disposed within a central opening in the toroidal permanent magnet. The first element may be a ferromagnetic material or a permanent magnet. Optionally, a second, toroidal shaped element may be movably disposed around the toroidal permanent magnet and a third, partial ring shaped element may be movably disposed around the second element. The second element and the third element may be permanent magnets or ferromagnetic materials.

As can be appreciated, the permanent magnets and elements may take any shape and may be positioned in a variety of different positions relative to each other (and the body) to modify the magnetic field in the patient's body, and the above embodiment is merely one example encompassed by the present invention.

Other aspects, objects and advantages of the invention will be apparent from the detailed description that follows.

BRIEF DESCRIPTION OF THE DRAWINGS

FIGS. 1A and 1B illustrate some radiation systems encompassed by the present invention.

FIG. 1C schematically illustrates a radiation system that encompasses the present invention.

DETAILED DESCRIPTION OF THE INVENTION

Figure 2A:
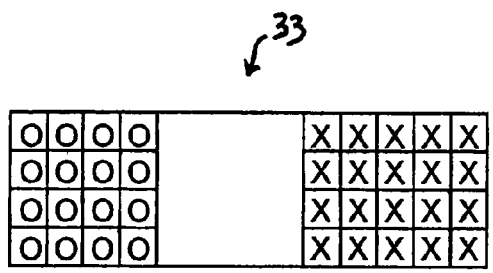
FIGS. 2A and 2B are cross-sectional views of a conventional coil magnet and a permanent magnet, respectively, in which the coil magnet and permanent magnet of substantially equal dimension produce substantially similarly shaped magnetic fields.

FIGS. 1A to 1C illustrate a radiation system 10 encompassed by the present invention. Radiation system 10 comprises a beam source 12 that generates a beam of high energy particles 14 along a beam path 16. Beam path 16 is directed toward a target area of patient's body 18. The patient's body 18 is situated on a patient support 20. The target area is typically a tumor, or the like. A computer controller (not shown) controls the initiation and movement of the beam source 12 and/or patient support 20. Optionally, monitoring detectors (not shown) may be included in the system.

Beam source 12 can be any conventional or proprietary source of high energy particles. Typically, beam source 12 is an electron beam source or a photon beam source. The high energy particles 14 enter the patient's body 18 and interacts with the tissue in a well understood manner. In particular, the high energy particles interact with the electrons in the tissue and the interaction results in electrons and positrons that carry the energy from the high energy particles from the beam. These high energy particles are mostly responsible for the ionization within the tissue along the beam path. The angular distribution of the electrons initially depends on the energy of the beam's high energy particles 14, but scattering and interactions lead to an electron-photon cascade. The cascade generates a "cloud" of ionizing particles that becomes broader and diffusive as it goes through the body tissues.

These effects have two results that impact the effectiveness of radiation treatment with high energy beams, such as for example a photon beam. First, the initial photon beam target area is not well circumscribed, being mostly dependent on the density of the tissue in its path, and on attenuation, e.g., less of the high energy particle beam is left the deeper it penetrates into the patient's body 18. Second, the cascade responsible for the tissue ionization further results in an undesired dose delivery downstream of the target area, as well as outside the beam boundary.

As shown in FIG. 1C, to increase the magnetic field at target area 28 within the patient's body 18, a permanent magnet assembly 23 that comprises one or more permanent magnets 24 may be positioned adjacent the patient's body 18 and beam path 16 so as to generate a magnetic field 26 that enhances the dose of high energy particles delivered to a target area 28 (e.g., a tumor) of the patient's body 18, as compared to the immediately surrounding regions 30 (e.g., tissue immediately around the tumor) and non-adjacent region 32 of the patient's body (e.g., entrance dosage on the patient's skin) along the beam path 16.

The permanent magnet(s) 24 may be used to affect the path of the charged particles within the patient's body that are created by the beam of high energy particles 14 emitted from the energy source 12. The magnetic field 26 from the appropriately positioned permanent magnet will cause the electron cascade to move in a more controlled corkscrew motion along the magnetic field lines.

Positioning the permanent magnet(s) 24 so that the magnetic field 26 is directed in a direction parallel to the beam path 16 will limit radial diffusion of electrons, and make the radial dose profile of the beam of high energy particles 14 more closely conform to the beam cross-sectional shape. Alternatively, a magnetic field 26 that is transverse to the beam path 16 will have less effect on radial profiles (e.g., one direction will be shielded and another will be enhanced), but will tend to reduce dose buildup downstream from the target area. As can be appreciated, a magnetic field 26 that is at more than 0-degree angle with respect to beam path 16 direction and is angled less than 90 degrees with respect to the transverse plane of the beam path 16, will produce some confinement along the beam path 16 and some confinement along transverse directions, but will allow some dose to "leak" along the field direction.

Figure 2B:
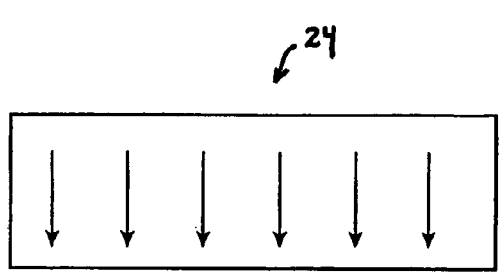

As shown in FIGS. 2A and 2B, a similarly sized superconductive coil magnet 33 and a permanent magnet 24 will create substantially similarly shaped magnetic fields. As can be appreciated, the superconductive coil magnet 33 will also requires a cooling system, insulation, a vacuum cryostat, etc., and the magnet assembly will have a much larger overall size than the permanent magnet. Moreover, because a permanent magnet 24 is an inert block of material and can be formed in any shape and then magnetized or can be manufactured from previously magnetized tiles or blocks, the permanent magnets of the present invention has an ease of use and flexibility that are not provided by a superconductive coil winding magnet.

A permanent magnet may be configured to duplicate the fields produced by the superconductive winding magnet 34, but does not require cooling or insulation, and can therefore be reconfigured easier. Moreover, without the cooling requirements, the permanent magnet can easily be used closer to and/or within a patient's body. Furthermore, because the permanent magnets are merely blocks of material, the shape of the material may be manufactured to create the desired magnetic field. Since the permanent magnets are unconstrained by winding limitations, cooling, and insulators, permanent magnets are maintenance free, are incapable of failure, and easy to reconfigure around the patients body.

If it is desired to reconfigure or change the magnitude (e.g., size and/or direction) of the magnetic field created by the permanent magnet(s) 24 an operator can either (1) move the entire permanent magnet assembly relative to the beam path, (2) move a first permanent magnet relative to a second permanent magnet, and/or (3) move a ferromagnetic element (e.g., iron) relative to the permanent magnet. Furthermore, if the permanent magnet assembly is mounted on a frame composed of a ferromagnetic material, it may be possible to use the frame to shape the magnetic field and change the magnitude of the magnetic field, as desired.

The permanent magnet(s) 24 of the present invention may be composed of a variety of different materials. In one exemplary embodiment, the permanent magnet 24 may comprise NdFeB (known by the trade name of Neomax). The Neomax magnets reach magnetic fields of 5 Tesla, but is typically between about 2 Tesla and about 4 Tesla. As can be appreciated, the permanent magnets 24 of the present invention can be comprise other materials, such as Alnico, SmCo, ferrites, and the like.

The permanent magnet assembly 23 encompassed by the present invention may comprise a variety of elements and may be disposed in any position relative to the beam path 16 and the patient's body 18, but preferably not directly in the beam path 16 unless a provision is made for the beam to pass unimpeded through the magnet, e.g., a hole. While the remaining discussion describes a plurality of different configurations of the permanent magnet assembly, it should be appreciated that such embodiments are merely examples and should not be construed to limit the scope of the present invention.

Figure 3:
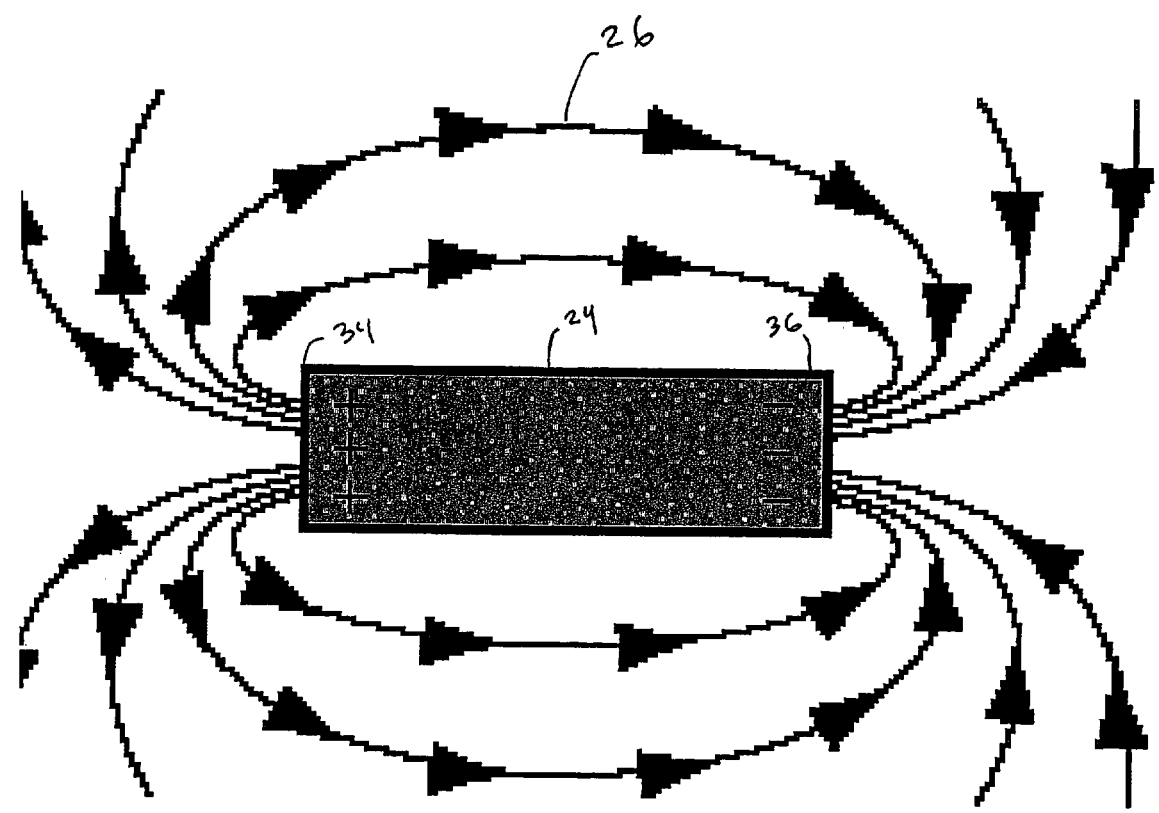
FIG. 3 illustrates a dipole magnetic field produced by a permanent magnet of the present invention.

As shown in FIG. 3, in one embodiment, the permanent magnet assembly 23 may comprise a single permanent magnet 24 that has a positive pole 34 and a negative pole 36 and the magnetic field 26 will extend between the positive pole 34 and the negative pole 36 as shown by the magnetic field lines 26. As will be described below, mere rotation and/or translation of the permanent magnet 24 can re-orient the magnetic field 26 to different orientations relative to the high energy particle beam 14 and the patient body 18.

Figure 4:
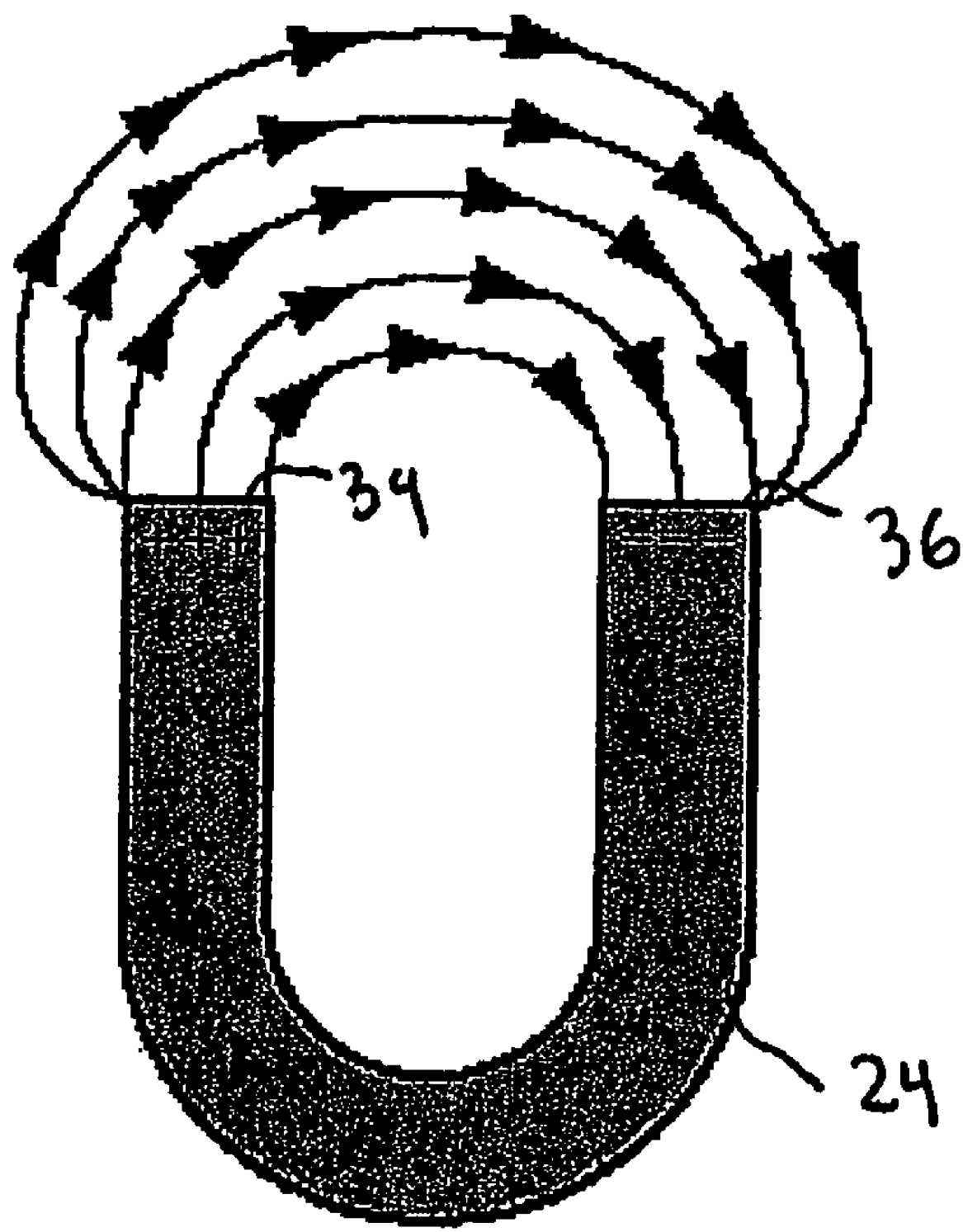
FIG. 4 illustrates a U-shaped permanent magnet and the resultant magnetic field.

FIG. 4 illustrates a U-shaped permanent magnet 24, in which the positive pole 34 is at one end of the U shape, and the negative pole 36 is on the opposite end of the U shape. As can be appreciated, the shape difference between FIG. 3 and FIG. 4 of the permanent magnet 24 will modify the field strength, direction, and the magnetic field gradient at different points in space. Depending on how the magnet is oriented in regards to the patient, the magnetic field 26 extends from the permanent magnet in such a way that it may result in transverse or longitudinal magnetic fields with respect to the longitudinal axis 38 of the patient 18.

The one or more permanent magnets 24 may be movable so as to vary the spatial location of the magnetic field relative to the beam path 16 and patient body 18 so as to adjust the magnetic dipole field components within the patients' body 18. As noted above, adjustment of the magnetic field can therefore increase the magnetic field at desired locations (e.g., target area) within the patient body.

Figure 5:
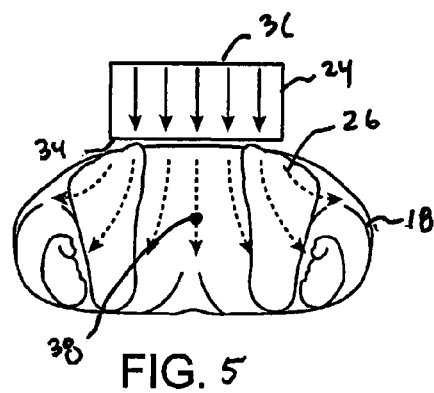
FIG. 5 is an end view of simplified embodiment encompassed by the present invention in which a permanent magnet is positioned and oriented to produce a magnetic field in a patient.
Figure 6A:
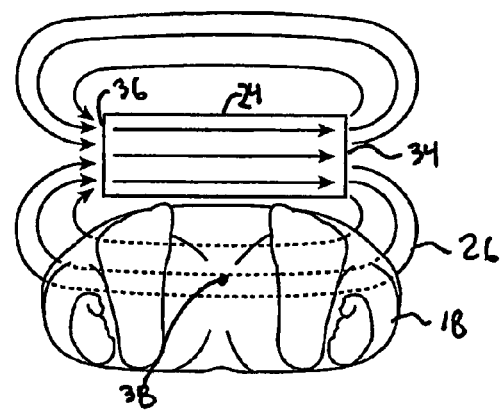
FIG. 6A illustrates a rotation of the permanent magnet in FIG. 3 so as to produce a magnetic field along a direction that is substantially transverse to a longitudinal axis of the patient.
Figure 6B:
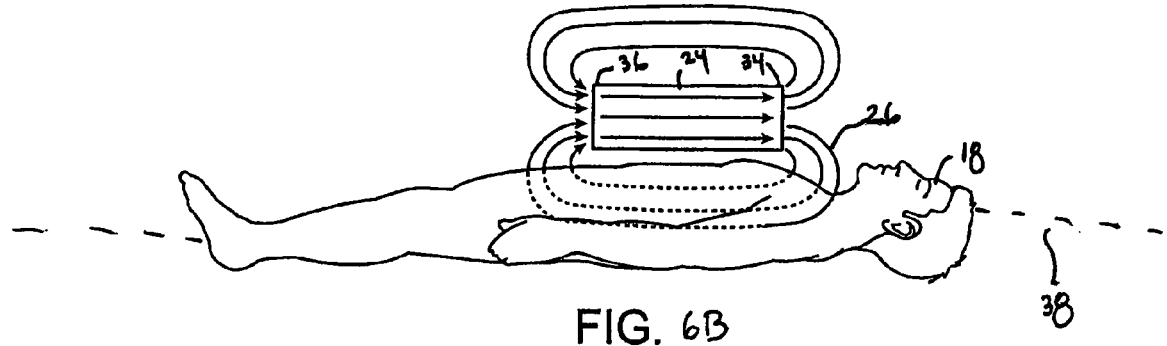
FIG. 6B illustrates rotation of the permanent magnet of FIG. 3 so as to produce a magnetic field along a direction that is substantially parallel to the longitudinal axis of the patient.

As shown in FIG. 5 a permanent magnet 24 may be positioned adjacent the patient's body 18 to produce a loop-like magnetic field 26 in patient's body 18. If it is desired to modify the orientation of the magnetic field, the operator need only move the permanent magnet relative to the patient's body. For example, as shown in FIG. 6A, if it is desired to produce a magnetic field that is substantially orthogonal to a longitudinal axis 38 of the patient, an operator could position a permanent magnet (e.g., that is magnetized along its longitudinal axis) in which the negative and positive poles of the permanent magnet are oriented on an axis that is substantially orthogonal to the longitudinal axis 38 of the patient. As shown in FIG. 6B, if it is desired to produce or modify the magnetic field so that the magnetic field is directed in a direction that is parallel to a patient's longitudinal axis, the positive and negative poles should be reoriented to an axis that is substantially parallel with the longitudinal axis 38 of the patient.

As can be appreciated, the permanent magnet assembly 23 may be positioned anywhere around the patient's body 18 so as to produce any desired magnetic field orientation. For example, one or more rings of permanent magnets may be positioned around the patient's entire body. The permanent magnet can be positioned anywhere around (or in) the body so as to create dose enhancement, as long as the permanent magnet is not directly in the path of the high energy particle beam.

Figure 7A:
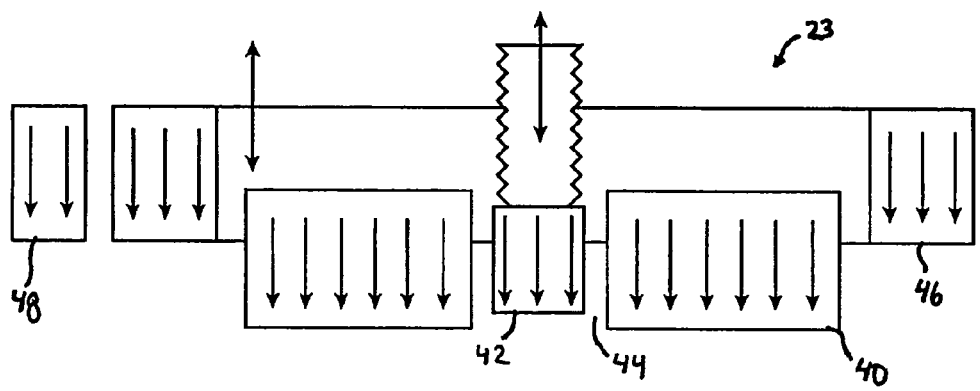
FIG. 7A is a cross-sectional view of one specific configuration of permanent magnets and elements that may be used to vary the magnitude of a magnetic field.
Figure 7B:
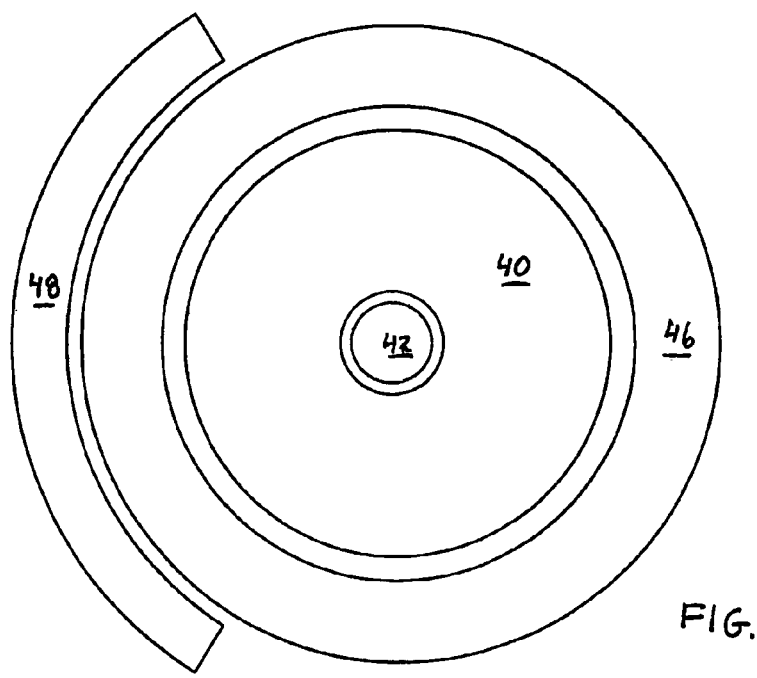
FIG. 7B is a top view of the configuration of permanent magnets of FIG. 7A.

FIGS. 7A and 7B illustrates one configuration of a permanent magnet assembly 23 encompassed by the present invention. As shown in FIG. 7A, the illustrated embodiment comprises a permanent magnet 40 and a first element 42. In the particular embodiment shown, the permanent magnet is in the form of an annular ring (toroid) that comprises an opening 44. The first element may be cylindrical shaped (or another shape) and be disposed within opening 44. In one configuration, both the permanent magnet 40 and first element 42 are permanent magnets. In another configuration, the first element is comprised of a ferromagnetic material. In an alternative embodiment, element "40" is comprised of a ferromagnetic material, and the first element is a permanent magnet.

In any of the configurations, the permanent magnet assembly 23 is movable relative to the beam path 16 and the patient's body 18, and the permanent magnet 40 and first element 42 are movable relative to each other. Having at least one of the permanent magnet 40 and the first element 42 movable allows for reconfiguration of the shape and strength produced by the permanent magnet assembly 23, and hence a subsequent adjustment of the dose in a target area of the patient's body. Moving the smaller, first element 42 relative to the beam path causes a small adjustment in the magnetic field. In contrast, moving the larger permanent magnet 40 creates a larger adjustment in the magnetic field in the patient's body. Consequently, the movement of the first element and/or the permanent magnet will depend on the desired effect of the magnetic field at the target area 28 of the patient's body 18.

The permanent magnet assembly 23 of FIGS. 7A and 7B may optionally include a second element 46. The second element 46 can take any shape, but in the illustrated embodiment, the second element is in the form of an annular ring that is concentrically positioned around the permanent magnet 40. The second element 46 may be a permanent magnet or a ferromagnetic material. Similar to the permanent magnet 40 and first element 42, the second element may be movable relative to the patient's body 18 and the other elements 40, 42 to change the magnetic field in the patient's body 18.

Optionally, the permanent magnet assembly 23 may also comprise a third element 48 that is asymmetrically disposed around the permanent magnet 40. In some configurations, the permanent magnet assembly 23 comprises the permanent magnet 40, first element 42, second element 46, and the third element 48, but in other configurations, the permanent magnet assembly only comprises less than all of the elements 40, 42, 46, 48. As is shown in FIGS. 7A and 7B, the third element may be a permanent magnet or it may be a ferromagnetic material. In the illustrated embodiment, the third element 48 is a partial ring so as to provide an asymmetrical magnetic field.

As can be appreciated, the present invention is not limited to the illustrated shapes (toroids, cylinders, partial rings) of FIGS. 7A and 7B, and any combination of shapes and relative geometries may be used with the present invention. For example, the elements may be blocks, rectangular, elliptical, spherical, triangular, other symmetrical shaped, or other asymmetrical shapes. Moreover, any number of elements may be incorporated into the permanent magnet assembly 23, and additional elements (e.g., fifth element, sixth element . . . nth element) or fewer elements may be used with the present invention.

The permanent magnet(s) 24 may be moved in a variety of ways. For example, the permanent magnets 24 are typically coupled to a floor mounted support and may be movable in any number of degrees of freedom. The position of the permanent magnets will depend on the position of the energy source, and the target area within the patients body. The permanent magnets may be manually moved, coupled to mechanical devices (e.g., screws or sliders), or it may be moved through stepper motors or hydraulic pistons, or other computer controlled assemblies. If desired, movement of the permanent magnet(s) 24 may be synchronized to a movement of the beam source 12.

Figure 8A:
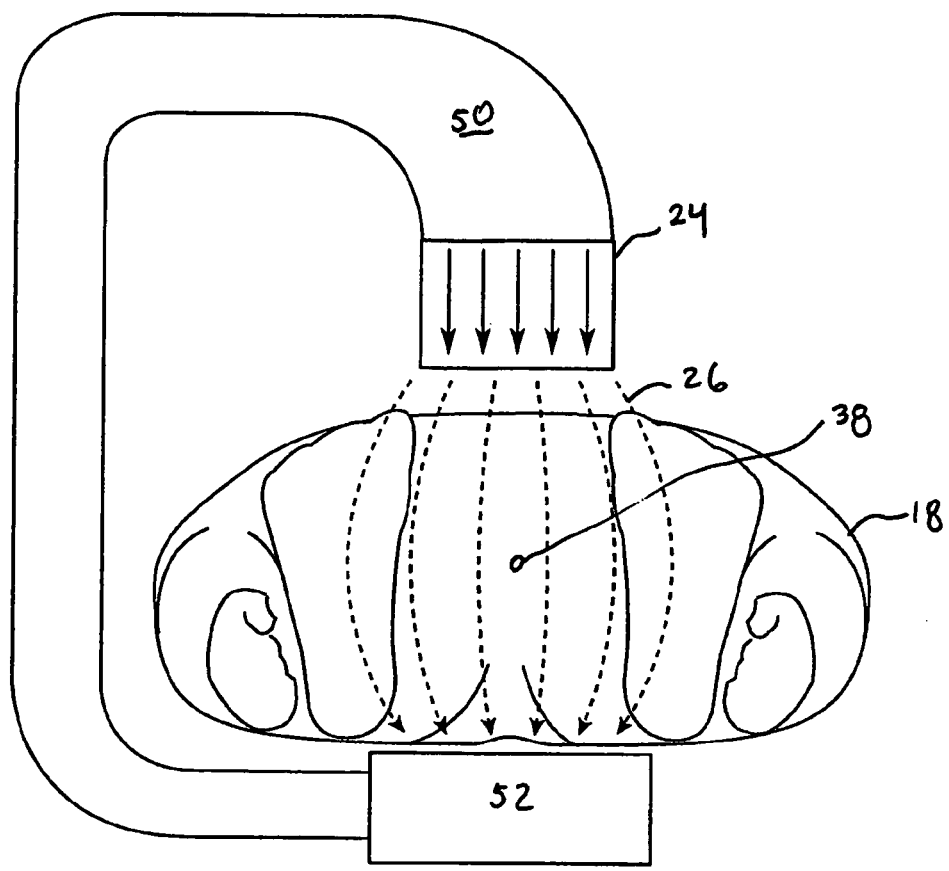
FIG. 8A is an end view of a simplified system in which a pole piece and permanent magnet assembly is positioned on substantially opposite sides of the patient.

FIG. 8A illustrates yet another embodiment encompassed by the present invention. FIG. 8A illustrates a support assembly 50 that positions a permanent magnet 24 adjacent a patient's body 18 that is positioned on a patient support (not shown). The support assembly 50 may be composed of a ferromagnetic material, such as iron, so as to help concentrate the magnetic field 26 from the permanent magnet 24. In the illustrated embodiment, the support assembly is a C-arm or U-arm so as to position a pole piece 52 on an opposite side of the patient from the permanent magnet 24. The pole piece 52 can be made of a permanent magnet or of a ferromagnetic material (e.g., iron). As shown in FIG. 8A, the pole piece 52 directs the magnetic field 52 in a direction that is substantially orthogonal to a longitudinal axis 38 of the patient's body 18. As can be appreciated, while the permanent magnet 24 is shown being above the patient's body and the pole piece 52 being below the patient's body, the permanent magnet 24 and pole piece 52 can be at any position and orientation relative to the patient's body. For example, in other embodiments, the permanent magnet 24 may be floor mounted below the patient and the pole piece may be movably positioned above the patient's body.

Figure 8B:
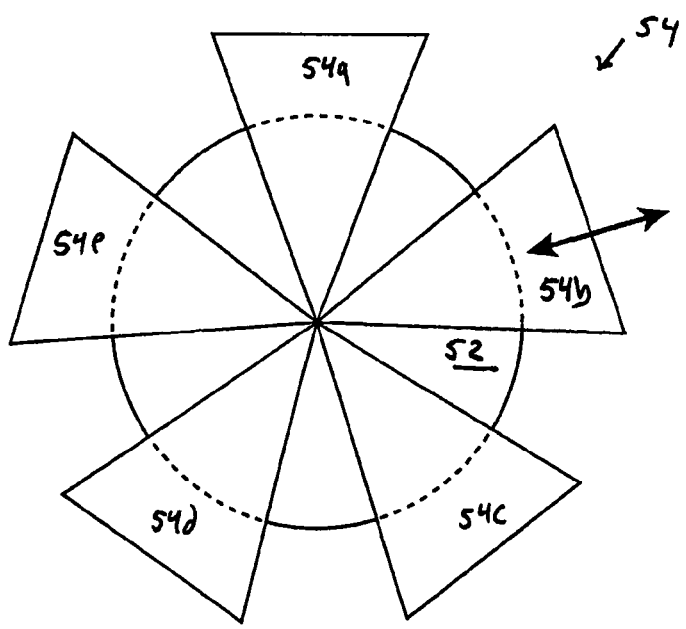
FIG. 8B illustrates one exemplary embodiment of a pole piece that comprises permanent magnets or ferromagnetic material.

FIG. 8B illustrates one embodiment of a pole piece 52 of the present invention. In the illustrated embodiment, the pole piece comprises a plurality of triangular or wedge shaped elements 54 (54a, 54b, 54c, 54d, 54e). At least some of the wedge shaped elements 54 are movable (either manually movable, mechanically movable, or computer controlled) in the direction of arrows either in conjunction with the other wedge shaped elements and/or independently of the other wedge shaped elements. The wedge shaped elements 54 may be a permanent magnet or it may be composed of a ferromagnetic material. While five elements 54 are shown, it should be appreciated that any number of elements 54 may be provided, and they may be provided in any shape.

In use, the permanent magnet assembly 23 may be positioned adjacent the patient's body 18 and beam path 16 in a configuration that provides a known magnetic field and dose enhancement. The beam source 12 is activated to deliver the beam of high energy particles 14 along the beam path 16 to the patient's body 18. The orientation and position of the permanent magnet assembly 23 will generate a dose enhancement at the target area 28 compared to the immediately surrounding regions 30 or the non-adjacent regions 32 along the beam path 16. If it is desired to adjust the magnetic field 26 relative to the beam path 16, for example, so as to treat another tumor or second target area, the permanent magnet assembly 23 may be reconfigured to generate a different magnetic field. As described above, reconfiguration of the magnetic field is typically carried out by repositioning a permanent magnet 24 or a ferromagnetic element of the permanent magnet assembly 23 or by repositioning the entire permanent magnet assembly 23. Reconfiguration of the magnetic field may be carried out with a computer controller or manually by an operator. The reconfiguration may be carried out as many times as desired during the radiation therapy.

Optionally, the operator may wish to synchronously move the permanent magnet assembly 23 with the beam source 12 so as to maintain the relative position between the magnetic field 26 and the beam path 16. In such embodiments, the controller may be programmed to synchronize the movement of the beam source 12 and the permanent magnet assembly 23.

In addition to positioning the permanent magnet around the patient's body 18, it may be possible to insert a permanent magnet 24 in the person's body. Insertion of the permanent magnet 24 into the body can be used to protect certain portions of the patient's body during radiation therapy. Protection occurs closest to the permanent magnet (s), where the field and gradients are strongest, thus excluding electrons. Protection extends roughly for an extent comparable to the size of the magnet, so it is desirable to position the magnet(s) as close as possible to the area to be protected. Superconductive coil magnets, (which require near absolute zero temperatures, insulation and vacuum) could cause irreparable damage if inserted into the patient's body. Damage could occur either through a leakage of the coolant or heating of the body tissues if the coil becomes normal conducting (e.g., a quench). In contrast, the permanent magnets of the present invention do not require cooling, insulation or leads and may be inserted into the body without such concerns. The permanent magnets 24 would typically only need a biologically compatible coating (e.g., inert plastic sleeve).

Figure 10:
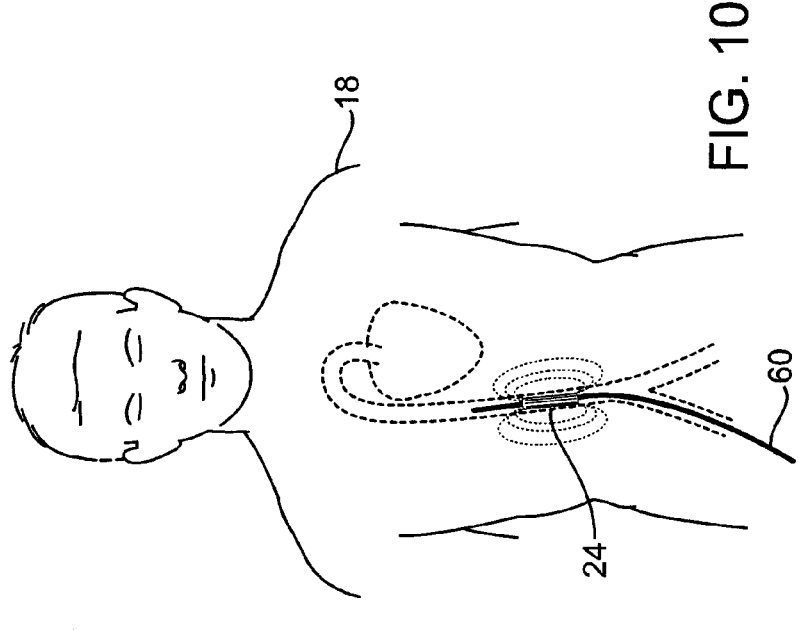
FIG. 10 illustrates an internal vascular magnet that is introduced into a vessel to protect the adjacent vascular walls.
Figure 9:
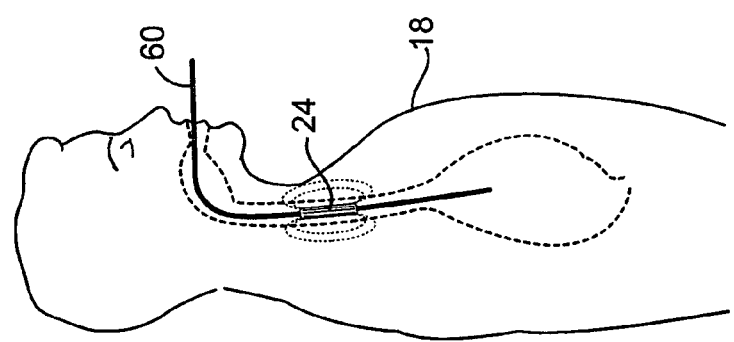
FIG. 9 illustrates an internal esophageal magnet that is introduced into the esophagus to protect the esophageal wall.
Figure 11:
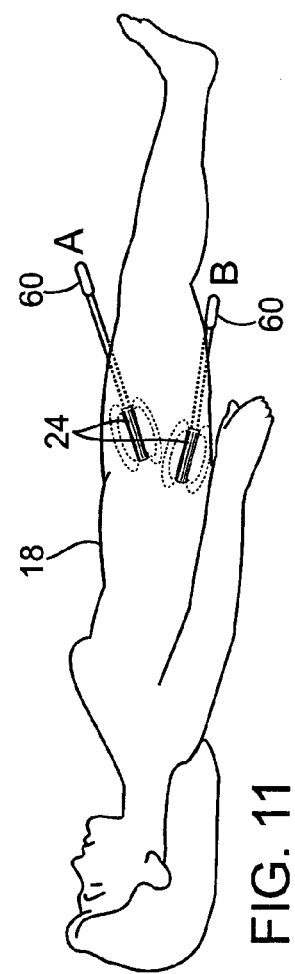
FIG. 11 illustrates an internal vaginal magnet that is introduced into the vaginal wall, and portions of the uterus and colon and an internal rectal magnet used to protect the wall of the rectum.

FIGS. 9 to 11 illustrate a variety of methods of positioning one or more permanent magnets 24 in the patient's body. A permanent magnet assembly may be coupled to a flexible catheter or relatively rigid probe 60. The catheter or probe 60 may be inserted into the appropriate body lumen (e.g., mouth, esophagus, vagina, rectum, colon, vascular lumen) and advanced to a desired area so as to position the permanent magnet assembly adjacent a target area. The permanent magnet assembly may comprise a combination of permanent magnets 24 and/or ferromagnetic materials.

The permanent magnet assembly may comprise at least one permanent magnet. The permanent magnet 24 may be symmetrical (such as a long cylinder-shaped magnet) or asymmetrically shaped and positioned within the probe 60. Alternatively, the permanent magnet assembly may comprise a plurality of symmetrical or asymmetrical permanent magnets that are mounted in or on the probe 60. Advantageously, the plurality of permanent magnets may be spaced from each other so as to allow flexibility in the catheter or probe 60 to allow the magnets to be advanced through a tortuous body lumen to the target area.

The positioning and orientation of the magnet poles 34, 36 of the permanent magnet 24 will depend on the desired magnetic field orientation within the body lumen. The poles may be positioned substantially orthogonal to a longitudinal axis of the catheter 60, the poles may be positioned substantially aligned with the longitudinal axis of the catheter 60, or the poles may be positioned at some other angle relative to the longitudinal axis of the catheter 60. One preferred embodiment has the poles positioned so that they are as far away from each other as the probe allows.

If desired, at least some of the permanent magnet(s) 24 may be movable relative to the other permanent magnets of the catheter 60. In addition to the permanent magnets 60, it may be desirable to have ferromagnetic elements (not shown) disposed within the catheter 60. The ferromagnetic elements may be fixed or movable.

It is understood that the examples and embodiments described herein are for illustrative purposes only and that various modifications or changes in light thereof will be suggested to persons skilled in the art and are to be included within the spirit and purview of this application and scope of the appended claims. Numerous different combinations are possible, and such combinations are considered to be part of the present invention.

What is claimed is:

1. A radiation treatment system comprising:
    a beam source that generates a beam of high energy particles along a beam path directed toward a body; and
    a permanent magnet assembly that comprises at least one permanent magnet positionable proximate to a target area of a body of a patient so as to generate a magnetic field in the target area of the body that causes an increase in the ratio of radiation dose delivered to the target area of the body compared to surrounding regions or to other regions of the body along the beam path.

2. The system of claim 1 wherein the beam source comprises an electron beam source or a photon beam source.

3. The system of claim 1 further comprising a movement controller coupled to the beam source and the permanent magnet assembly, wherein the movement controller is adapted to synchronously move the at least one permanent magnet with a movement of the beam source so as to maintain the relative position between the at least one permanent magnet and the beam path.

4. The system of claim 1 further comprising a movement controller coupled to the permanent magnet assembly, wherein the movement controller is adapted to rotate the permanent magnet assembly about one or more axes so as to modify the magnitude of the magnetic field in the target area of the body.

5. The system of claim 1 wherein the at least one permanent magnet comprises a plurality of permanent magnets, wherein at least one of the plurality of permanent magnets is movable relative to the other permanent magnets,
    wherein movement of the at least one permanent magnet adjusts the geometry of the permanent magnet assembly and adjusts the magnitude of the magnetic field at the target area from the plurality of permanent magnets.

6. The system of claim 1 further comprising means for varying a size, strength and direction of the magnetic field.

7. The system of claim 1 wherein the permanent magnet assembly comprises:
    the permanent magnet; and
    a first element positioned adjacent the permanent magnet,
    wherein movement of at least one of the first element and the permanent magnet relative to the body changes at least one of a size and strength of the magnetic field in the target area of the body.

8. The system of claim 7 wherein the permanent magnet is toroidal shaped, and the first element is positioned within a central opening in the first toroidal permanent magnet,
    wherein the first element comprises a cylindrical permanent magnet or a cylindrical piece of ferromagnetic material.

9. The system of claim 8 further comprising a second element movably and concentrically disposed around the first toroidal permanent magnet,
    wherein the second element comprises toroidal permanent magnet or a toroidal shaped piece of ferromagnetic material.

10. The system of claim 9 further comprising a third, partial ring element radially disposed around the second element,
    wherein the third, partial ring element comprises a permanent magnet or ferromagnetic material.

11. The system of claim 1 wherein the at least one permanent magnet comprises a plurality of round, rectangular, triangular, or elliptical shaped permanent magnets.

12. The system of claim 1 wherein the at least one permanent magnet(s) is coupled to a support assembly.

13. The system of claim 12 wherein the support assembly positions the at least one permanent magnet on one side of the body and a pole piece on a substantially opposite side of the body.

14. The system of claim 13 wherein the pole piece comprises a permanent magnet or a ferromagnetic material.

15. The system of claim 13 wherein the pole piece comprises a plurality of movable elements, wherein movement of the one or more of the plurality of movable elements adjusts the magnitude of the magnetic field.

16. The system of claim 15 wherein the plurality of movable elements comprise substantially pie-shaped or triangular shaped pieces of ferromagnetic material.

17. The system of claim 1 wherein the at least one permanent magnet comprises a single magnet that produces a dipole field in the body.

18. The system of claim 17 wherein the single magnet comprises a configurable geometry so as to allow for modification of the dipole field in the body.

19. The system of claim 1 wherein the at least one permanent magnet comprises NdFeB, Alnico, SmCo, or ferrites.

20. The treatment system of claim 1 where the permanent magnet is introduced into the body.

21. A method of enhancing target radiation dose in medical treatments, the method comprising:
directing a high energy particle beam at a body along a beam path; and
orienting a permanent magnet assembly that comprises at least one permanent magnet adjacent a target tissue in a body of a patient so as to create a magnetic field component in the target tissue of the body, wherein the magnetic field component in the target tissue created by the at least one permanent magnet enhances the ratio of radiation dose in a target area of the body, compared to surrounding regions or in other regions of the beam along the beam path.

22. The method of claim 21 wherein directing the high energy particle beam comprises directing an electron beam or directing a photon beam.

23. The method of claim 21 further comprising rotating the permanent magnet assembly synchronously with a rotation of the beam source so as to maintain the relative positions between the beam path and the permanent magnet assembly.

24. The method of claim 21 comprising modifying the magnetic field relative the beam path.

25. The method of claim 24 wherein modifying the magnetic field is carried out by moving the permanent magnet assembly relative to the beam path.

26. The method of claim 24 wherein the permanent magnet assembly comprises a first permanent magnet and a first element, wherein modifying the magnetic field comprises moving at least one of the first element and the first permanent magnet relative to the body.

27. The method of claim 26 wherein the first element comprises a ferromagnetic material or a second permanent magnet.

28. The method of claim 26 wherein the first permanent magnet comprises a toroidal permanent magnet and the first element comprises a cylindrical body disposed within a central opening of the toroidal permanent magnet.

29. The method of claim 28 wherein the permanent magnet assembly comprises a movable second element disposed around the first toroidal permanent magnet,
wherein the second element comprises a movable permanent magnet or a ferromagnetic material.

30. The method of claim 29 wherein the permanent magnet assembly comprises a movable third element in the form of a partial ring element,
wherein the third element comprises a movable permanent magnet or ferromagnetic material.

31. The method of claim 21 wherein the permanent magnet assembly comprises a single permanent magnet, wherein the single permanent magnet creates a dipole field in the body.

32. The method of claim 31 wherein the single permanent magnet comprises a configurable geometry.

33. The method of claim 31 comprising modifying the magnetic field by rotating the single permanent magnet relative to the beam path.

34. The method of claim 33 wherein rotating the single permanent magnet positions the magnetic field in an orientation that is substantially parallel with a longitudinal axis of the body.

35. The method of claim 33 wherein rotating the single permanent magnet positions the magnetic field in an orientation that is substantially orthogonal with a longitudinal axis of the body.

36. The method of claim 21 comprising:
positioning the permanent magnet assembly on a first side of the body with a support assembly; and
positioning a pole piece on the support assembly on a substantially opposite side of the body.

37. The method of claim 36 wherein the support assembly comprises ferromagnetic material.

38. The method of claim 36 wherein the pole piece comprises a permanent magnet or a ferromagnetic material.

39. The method of claim 38 wherein the pole piece comprises a plurality of movable elements adjacent the pole piece, the method further comprising moving one or more of the plurality of movable elements relative to the pole piece to concentrate or widen the magnetic field within the body.

40. The method of claim 39 wherein the plurality of movable elements comprise substantially pie shaped or triangular shaped pieces of ferromagnetic material or permanent magnet material.

41. The method of claim 21 wherein the at least one permanent magnet comprise NdFeB, Alnico, SmCo, or ferrites.

42. The method of claim 21 where the permanent magnet is introduced into the body.

43. A radiation treatment system comprising:
means for generating a beam of high energy particles along a beam path directed toward a body; and
permanent magnet means for generating a magnetic field in a desired target area of a body of a patient so as to cause a dose enhancement in the desired target area of the body, compared to surrounding regions or in other regions of the beam along the beam path.

* * * * *